United States Patent [19]

Drake

[11] 4,217,303
[45] Aug. 12, 1980

[54] PREPARATION OF UNSATURATED NITRILES

[75] Inventor: Charles A. Drake, Bartlesville, Okla.

[73] Assignee: Phillips Petroleum Company, Bartlesville, Okla.

[21] Appl. No.: 32,975

[22] Filed: Apr. 24, 1979

[51] Int. Cl.$^2$ .................. C07C 120/00; C07C 121/46; C07C 121/20; C07C 121/66
[52] U.S. Cl. ............................ 260/465.8 R; 260/464; 260/465 H; 260/465 K; 260/465.9
[58] Field of Search ............. 260/464, 465.8 R, 465.9, 260/465 K, 465 H

[56] References Cited

U.S. PATENT DOCUMENTS

| | | | |
|---|---|---|---|
| B 456,900 | 2/1976 | Turk et al. | 260/464 |
| 2,641,607 | 6/1953 | Albisetti et al. | 260/465.3 |
| 3,296,108 | 1/1967 | Hutson et al. | 204/163 |
| 3,652,642 | 3/1972 | Baba | 260/465.8 D |
| 3,840,583 | 10/1974 | Turk et al. | 260/465.8 R |
| 3,883,606 | 5/1975 | Banks | 260/465.9 X |
| 3,898,268 | 8/1975 | Drake | 260/465.9 |
| 3,929,860 | 12/1975 | Drake | 260/465.9 |
| 3,985,786 | 10/1976 | Drake | 260/465.8 R |
| 4,117,001 | 9/1978 | Fozzard | 260/465.8 R |
| 4,117,002 | 9/1978 | Drake | 260/465.9 X |

OTHER PUBLICATIONS

MacDonald et al., Chem. Eng. Progress, 47, pp. 363–369 (1951).
Albisetti et al., J.A.C.S., 78, (1956), pp. 2637–2641.
Chemical Engineers Handbook, 5th Ed., pp. 4-20 to 4-22, (1973).

*Primary Examiner*—Joseph Paul Brust

[57] ABSTRACT

An olefinically unsaturated nitrile, an olefinic hydrocarbon containing an allylic hydrogen, and a monoadduct reaction product of an olefinic hydrocarbon and an olefinically unsaturated nitrile are contacted in a plurality of reactors in series in the presence of a diluent to produce unsaturated dinitriles. At least a portion of the olefinically unsaturated nitrile is added directly to at least one of the reactors other than the first reactor in the series to reduce the production of heavies having a boiling range greater than the unsaturated dinitrile. At least a portion of the diluent is added directly to at least one of the reactors other than the first reactor in the series to reduce the production of undesired middle byproducts having a boiling range between the monoadduct reaction product and the unsaturated dinitrile.

60 Claims, No Drawings

PREPARATION OF UNSATURATED NITRILES

This invention relates to the production of unsaturated dinitriles. In a specific aspect this invention relates to a reaction of an olefinically unsaturated nitrile, an olefinic hydrocarbon and a monoadduct of an olefinic hydrocarbon and an olefinically unsaturated nitrile a plurality of reactors in series in the presence of a diluent to yield olefinically unsaturated dinitrile products having a greater number of carbon atoms than the unsaturated nitrile reactant.

In U.S. Pat. No. 2,641,607 (issued June 9, 1953), Albisetti et al describe the thermal reaction of a 2-alkenenitrile (e.g. acrylonitrile) with a neutral olefinic compound (e.g. isobutylene) in a first stage reaction to produce unsaturated mononitriles having a greater number of carbon atoms (e.g. 5-methyl-5-hexenenitrile). Albisetti et al state that the reaction effluent can be distilled to recover the unsaturated mononitrile product, and that the recovered unsaturated mononitrile product can be thermally reacted with a neutral olefinic compound in a second stage reaction to produce unsaturated dinitriles. The patentees state that the first stage reaction can be conducted in the presence or absence of an inert diluent or solvent. The patent lists hydrocarbons, ethers and esters as suitable inert organic solvents, and then states that the reaction also takes place in the presence of water as a diluent, the water serving as a heat transfer medium.

In J. Am. Chem. Soc. 78, pp. 2637–2641 (1956), Albisetti et al describe further work with the thermal reaction of a 2-alkenenitrile with a neutral olefinic compound in a first stage and the subsequent reaction in a second stage of a neutral olefinic compound with the reaction product of the first stage to produce unsaturated dinitriles. The authors state that water can be employed as the reaction medium in the second stage reaction of acrylonitrile with 5-methyl-5-hexenenitrile to produce 5-methylenenonanedinitrile. The authors also state that in the case of polymerizable nitriles, the use of water as the medium prevented formation of tars.

In U.S. Pat. No. 3,840,583 (issued Oct. 8, 1974) Turk et al disclose that the yield of unsaturated dinitriles can be increased by contacting an unsaturated mononitrile, an olefin and a monoadduct reaction product of an unsaturated mononitrile and an olefin wherein the monoadduct reaction product is present in significant amount during substantially the entire reaction period. The patentees stated that this single stage reaction could be carried out in the presence or absence of a solvent or diluent which is nonreactive with either the reactants or the reaction products. The patentees list various hydrocarbons, various ethers, tetrahydrofuran, dioxane, carbon tetrachloride and methylene chloride as representative commercially available nonreactive solvents that can be employed.

In U.S. Pat. No. 3,985,786 (issued Oct. 12, 1976) Drake discloses that the utilization of an aqueous medium as the diluent in the Turk et al single stage process provides a greater increase in the yield of unsaturated dinitriles than would be expected from the summation of the increase in yield in unsaturated dinitriles achieved by the utilization of water as the diluent in both stages of the Albisetti et al process and the increase in yield in unsaturated dinitriles achieved by the utilization of the Turk et al single stage reaction instead of the Albisetti et al two stage process.

The reactions described in the referenced patents and publications result in the production of significant quantities of undesired heavies which have a boiling range greater than the unsaturated dinitrile which is the desired product. The undesired heavies consume reactants which results in lower economics for the overall process. It has now been discovered that, when a plurality of tank type reactors in series are utilized in the processes of Turk et al and Drake, introduction of a portion of the olefinically unsaturated nitrile directly to at least one of the tank type reactors other than the first reactor in the series, rather than introducing all of the olefinically unsaturated nitrile into the first tank type reactor in the series, results in a reduction of the production of undesired heavies.

The reactions described in the referenced patents and publications also result in the production of significant quantities of undesired middle byproducts which have a boiling range between the olefinically unsaturated dinitrile product and the monoadduct of an olefinic hydrocarbon and an olefinically unsaturated nitrile. The undesired middle byproducts consume reactants and also cause purification problems for the cleared reaction product. It has now been discovered that, when a plurality of tank type reactors in series are utilized in the processes of Turk et al and Drake, introduction of a portion of the diluent directly to at least one of the tank type reactors other than the first reactor in the series, rather than introducing all of the diluent into the first tank type reactor in series, results in a reduction of the production of undesired middle byproducts.

Accordingly, it is an object of this invention to provide an improved process for the reaction of an olefinic hydrocarbon and an olefinically unsaturated nitrile in order to obtain an olefinically unsaturated dinitrile reaction product having a greater number of carbon atoms than the original nitrile. Another object is to provide an improved process which results in increased yields of high carbon number olefinically unsaturated dinitrile reaction products. Yet another object of the invention is to decrease the production of undesired heavy byproducts. Yet another object of the invention is to decrease the production of undesired middle byproducts. Other objects, aspects and advantages of the invention will be apparent from a study of the specification and the appended claims to the invention.

Any unsaturated mononitrile can be employed in the practice of this invention provided the mononitrile contains ethylenic unsaturation, contains at least one hydrogen atom attached to a doubly bonded carbon atom, and contains a cyano group attached to a carbon atom adjacent and doubly bonded to a carbon atom which is attached to at least one hydrogen atom. Preferably the mononitrile reactant is free of acetylenic unsaturation and contains from 1 to 2 ethylenically unsaturated, nonconjugated double bonds as the sole aliphatic unsaturation, while the total number of carbon atoms in the mononitrile reactant is within the range of 3 to 18, more preferably within the range of 3 to 8. Illustrative unsaturated mononitrile reactants include those represented by the formula

wherein each R is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, such as alkylcycloalkyl, cycloalkylalkyl, aralkyl and arylcycloalkyl radicals. Examples of unsaturated nitriles meeting the requirements, of the above formula are acrylonitrile, methacrylonitrile, 2-decenenitrile, 3-cyclohexyl-2-propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2-nonenenitrile, and the like, and mixtures of two or more thereof.

Any acyclic or cyclic olefinic hydrocarbon compound can be employed in the practice of this invention, provided that the compound has at least one olefinic linkage having joined to one of the doubly bonded carbons a carbon atom having at least one hydrogen atom attached thereto, said doubly bonded carbon atoms being free of cyano groups attached thereto. The olefinic hydrocarbons preferably are free of acetylenic unsaturation and have from 3 to 18 carbon atoms per molecule with from 1 to 2 ethylenically unsaturated, nonconjugated double bonds as the sole aliphatic unsaturation. The preferred types of these compounds are the open chain monoolefinic hydrocarbons represented by the formula $$R'_2C=CR'-CHR'_2$$

wherein each R' is independently selected from the group consisting of hydrogen and hydrocarbyl radical. The hydrocarbyl radicals are preferably selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of olefinically unsaturated hydrocarbon compounds which are useful in the process of this invention include propylene, isobutylene, diisobutylene, triisobutylene, 1,5-hexadiene, beta-pinene, 1,5-cyclooctadiene, 2,4,4-trimethyl-1-pentene, 2-butene, biallyl, bimethallyl, alpha-methylstyrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1-phenyl-2-propene, and the like, and mixtures of two or more thereof.

Suitable monoadduct reactants include any monoadduct reaction product of an olefinic hydrocarbon, as hereinabove defined, and an unsaturated mononitrile, as hereinabove defined. It is believed that the olefinic hydrocarbon compound and the unsaturated mononitrile react in accordance with the "ene" reaction to produce, as the principal monoadduct reaction product, a compound having the structural formula

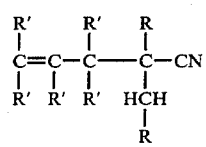

Generally, a lesser amount of an isomeric monoadduct reaction product having the formula

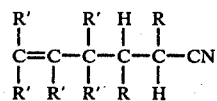

is also produced. Thus, isobutylene and acrylonitrile react to produce 5-methyl-5-hexenenitrile as the principal monoadduct reaction product along with a small amount of 2,4-dimethyl-4-pentenenitrile. It can be readily seen that isobutylene as the olefinic hydrocarbon reactant possesses six of the required allylic hydrogens but that all six are structurally equivalent so that only two monoadduct reaction compounds corresponding to the above general formulas are produced according to the "ene" reaction.

However, it will also be evident that if a compound having two or more allylic hydrogens which are not structurally equivalent is employed as the olefinic hydrocarbon reactant, the number of expected isomeric monoadduct reaction product compounds having the above general formulas will be increased. For example, if 2,4,4-trimethyl-1-pentene is reacted with acrylonitrile the major monoadduct reaction products expected according to the "ene" reaction would be 5-methylene-7,7-dimethyloctanenitrile and 4-methylene-2,6,6-trimethylheptanenitrile with lesser amounts of 5,7,7-trimethyl-5-octenenitrile and 4-t-butyl-5-methyl-5-hexenenitrile. Other factors not fully understood at present may influence the relative amounts of the possible isomers in the monoadduct reaction product and in other instances presently employed analytical methods may not distinguish the various isomers present. Indeed, the monoadduct reaction product finds utility in many applications with no need of a costly separation of the isomers present in the monoadduct reaction product. The isomeric mixture reaction product produced by the reaction of an olefinic hydrocarbon and an olefinically unsaturated nitrile can be employed as the monoadduct reactant, or one or more isomers can be separated from the isomeric mixture reaction product and such separated isomer or isomers can be employed as the monoadduct reactant. Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4-methyl-4-pentenenitrile, 2(n-butyl)-4-pentenenitrile, 2-(n-butyl)-5-phenyl-4-pentenenitrile, and mixtures of two or more thereof.

The diadduct reaction products obtained by the process of this invention comprise the reaction product mixtures formed by the monoaddition of an unsaturated mononitrile and any monoadduct reaction product. Exemplary of a diadduct reaction product is the reaction product mixture comprising the major isomer species 5-methylenenonanedinitrile and 5-methyl-4-nonenedinitrile, and minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

Any amount of olefinic hydrocarbon, olefinically unsaturated mononitrile and monoadduct reaction product can be employed in the practice of this invention. In general, the mol ratio of olefinically unsaturated mononitrile reactant to olefinic hydrocarbon reactant will be in the range of about 10:1 to about 0.1:1, preferably in the range of about 2:1 to about 0.3:1. In general, the monoadduct reaction product will be employed in an amount such that, during substantially the entire reaction period, the net monoadduct reaction product present in the reaction mixture will constitute from about 10 to about 90, preferably from about 20 to about 80, and more preferably from about 30 to about 70 weight percent of the total reaction mixture. The net amount of monoadduct reaction product present in the reaction zone is the sum of the amount of monoadduct reaction product charged to the reaction zone plus the amount of monoadduct reaction product produced by the reaction of the olefinic hydrocarbon reactant and the olefinically unsaturated mononitrile reactant in the reaction zone less the monoadduct reaction product consumed by reaction with the olefinically unsaturated mononitrile in the reaction zone to produce diadduct. The monoadduct reaction product charged to the reaction zone can be the same as or different from the monoadduct reaction product produced by the reaction of the olefinic hydrocarbon reactant and the olefinically unsaturated mononitrile reactant in the reaction zone, but it will be generally preferred for them to be the same. The total reaction mixture includes all fluid materials present in the reaction zone, i.e. reactants, diluents, products, byproducts, etc.

Any suitable tank reactor can be employed in the practice of the invention. The tank reactor is preferably equipped with some means for agitating the reactants in the tank. Any suitable number (at least two) of tank reactors can be employed in series in the practice of the invention. Three tank reactors in series are presently preferred.

Any suitable division of introduction of the fresh olefinically unsaturated nitriles among the plurality of tank reactors in series can be employed in the practice of the invention. Preferably, the fresh olefinically unsaturated nitrile is provided approximately equally to each of the reactors in the series of reactors. For the preferred series of three tank reactors, approximately one-third of the fresh olefinically unsaturated nitrile is provided to each of the three tank reactors.

Any suitable division of the diluent among the plurality of tank reactors in series can be employed in the practice of the invention. Addition of the diluent early provides better reaction conditions but also increases the production of undesired middle byproducts. It is thus preferred to provide approximately one-half of the fresh diluent to the first reactor in the series with the second half of the fresh diluent being provided to the second reactor in the series. However, the diluent could be provided equally or unequally to each of the reactors in the series of reactors if desired.

Any suitable reaction conditions for a continuous process can be employed in the practice of the invention. The reaction time employed in the practice of this invention can vary widely. The liquid hourly space velocity will generally be in the range of about 0.05 to about 20, preferably in the range of about 0.1 to about 10, more preferably in the range of about 0.5 to about 2.

The reaction temperatures that can be employed in the practice of the invention can vary widely. Generally, however, reaction temperatures are within the range of from about 100° C. to about 500° C., and preferred reaction temperatures are within the range of from about 200° C. to about 350° C.

The reaction pressures suited to the practice of this invention also vary widely. Reaction pressures within a range of from about atmospheric pressure to about 100,000 psig (690 MPa) can be employed; however, reaction pressures within the range of from about 500 psig (3.5 MPa) to about 4000 psig (2.75 MPa) are preferably employed.

If desired, the processes of this invention can be carried out in the presence of a polymerization inhibitor. The use of the inhibitor often advantageously limits side reactions such as the dimerization or polymerization of the olefinically unsaturated mononitrile. When an inhibitor is employed, it is generally desirable that an amount of from about 0.001 to about 5, preferably from about 0.1 to about 1, percent by weight inhibitor based on the weight of unsaturated mononitrile reactant be employed. Suitable inhibitors include hydroquinone, 2,6-di-tert-butyl-para-cresol, 2,6-di-tert-butylhydroquinone, 4-tert-butylcatechol, para-hydroxydiphenylamine, and the like, and mixtures of any two or more thereof.

The reaction of the above described olefinic hydrocarbon reactant, olefinically unsaturated mononitrile reactant and monoadduct reaction product reactant can be carried out in the presence of any suitable diluent. Preferably the diluent comprises at least 50 weight percent water, more preferably at least 80 weight percent water, and more preferably consists essentially of water. The codiluent with water, if employed, can be any solvent or diluent which is nonreactive with either the reactants or the reaction products. Examples of suitable codiluents include benzene, toluene, para-xylene, ortho-xylene, meta-xylene, ethylbenzene, diethyl ether, ethyl propyl ether, dibutyl ether, tetrahydrofuran, dioxane, cyclohexane, carbon tetrachloride, methylene chloride, and the like, and mixtures of any two or more thereof.

The diluent can be employed in any suitable amount. In general the diluent will be employed in an amount in the range of about 0.01 to about 40 parts by weight of total diluent per part by weight of olefinically unsaturated mononitrile reactant charged to the reaction zone. The amount of diluent currently preferred is in the range of about 0.1 to about 20 parts by weight of total diluent per part by weight of olefinically unsaturated mononitrile reactant charged to the reaction zone. The advantages of the aqueous diluent system include improved selectivity to the desired olefinically unsaturated nitrile and reduced amounts of heavy polymeric byproduct. This latter byproduct is particularly objectionable because it tends to foul reactor surfaces.

A convenient method of carrying out this invention comprises combining a fresh mixture of an olefinically unsaturated mononitrile (e.g. acrylonitrile), an olefinic hydrocarbon compound (e.g. isobutylene), and a monoadduct reaction product reactant (e.g. a mixture of 5-methyl-5-hexenenitrile and 2,4-dimethyl-4-pentenenitrile) with a fresh diluent fluid (water) and then introducing the combined mixture of reactants and diluent fluid into the initial reactor of a plurality of heated tank reactors in series. Additional quantities of the fresh olefinically unsaturated mononitrile is fed to each of the plurality of tank reactors other than the initial reactor in the series. Also additional quantities of the fresh diluent fluid is fed to each of the plurality of tank reactors other than the initial reactor in the series. The temperature of each of the plurality of tank reactors is maintained within the range of about 200° to about 250° C.; the pressure in each of the plurality of tank reactors is maintained at a pressure in the range of about 500 to about 4000 psig; the mol ratio of the olefinically unsaturated mononitrile to the olefinic hydrocarbon in the feed is maintained in the range of about 5:1 to about 0.2:1; the concentration of the monoadduct reaction product in the reaction mixture throughout the entire reaction zone constituted by the plurality of tank reactors is maintained in the range of about 20 to about 80 weight percent; and the liquid hourly space velocity throughout the entire reaction zone is maintained in the range of about 0.5 to about 2. The resulting olefinically unsaturated dinitrile reaction product, which is removed as the product from the last one of the plurality of tank reactors in series, is readily isolated from the reaction effluent mixture by any convenient product recovery method such as fractional distillation.

If desired, the reaction can be carried out in the presence of any suitable promoter, for example an organo derivative of a Group VA element defined by the following formula $$R'''_n ZH_{3-n}$$

wherein each R''' is independently selected from the group consisting of aryl, alkaryl, cycloalkylaryl, araryl, aryloxy, alkaryloxy, arylaryloxy; wherein each R''' group contains from 6 to 12 carbon atoms; Z is selected from the group consisting of N, P, P=O, As, Sb, or Bi; and n is 2 or 3. Illustrative of organo derivatives of the Group VA elements defined by the above formula are the following compounds: triphenylphosphine, diphenylphosphine, tris(hexylphenyl)phosphine, tris(cyclohexylphenyl)phosphine, dinaphthylphosphine, tris(4-biphenyl)phosphine, tris(4-butylphenyl)phosphine, triphenylamine, diphenylamine, tris(3,5-dipropylphenyl)amine, triphenylarsine, tris(pentylphenyl)arsine, triphenylbismuthine, diphenylarsine, diphenyl-4-biphenylphosphine, tris(p-tolyl)stibine, tris(3,5-dimethylphenyl)bismuthine, diphenyl(4-ethylphenyl)phosphine, diphenoxy(phenyl)phosphine, diphenyl(p-methylphenoxy)phosphine, triphenylphosphite, diphenyl(p-tolyl)phosphine, triphenylphosphate, and the like, and mixtures of any two or more thereof. The variant designated by n in mixtures of promoters represented by the formula R'''$_n$ZH$_{3-n}$ can vary, with the arithmetical sum of the value of n of individual promoters, from 2 to 3. The term "reaction promoting material" includes materials commonly called catalysts as well as materials commonly called promoters.

If employed, the amount of promoter utilized in the process of this invention can vary widely. In general, the mol ratio of promoter to unsaturated mononitrile reactant charged to the reaction zone would be in the range of about 1:20 to about 1:1. Preferably, the mol ratio of promoter to unsaturated mononitrile reactant charge would be in the range of about 1:10 to about 1:3.

The following examples are presented in further illustration of the invention but should not be unduly construed in limitation thereof.

EXAMPLE I

The following runs were conducted to illustrate the advantage of feeding part of the acrylonitrile directly to each reactor in the series rather than feeding the total acrylonitrile to the first reactor in the series. All runs were conducted at a reaction temperature of about 280° C. and at a pressure of abpit 2500 psig (17 MPa).

The reactor system was three 300 cc high pressure stirred autoclave reactors connected in series. All runs were continuous, with data being taken after the reactor had been lined out under simulated recycle conditions with return of the monoadduct to the reactor. The yield of monoadduct was obtained by subtracting the monoadduct fed into the reactors from the monoadduct in the effluent flowing from the reactors. Ideally, the net yield of monoadduct should be zero; however, this was not quite achieved in the runs.

For runs 1, 3 and 5 set forth in Table I, the approximate composition (weight percent) of the organic feed was:

| | |
|---|---|
| acrylonitrile (ACN) | 13 weight percent |
| isobutylene | 24 weight percent |
| monoadduct (MA) mixture of approximately 95 percent 5-methyl-5-hexene nitrile with approximately 5 percent 2,4-dimethyl-4-pentenenitrile | 63 weight percent |

All of the organic feed composition was fed into the first reactor in the series at a rate of 17.8 cc/minute. Water was fed to only the first reactor in series at a rate of 0.75 cc/minute in run 1. The flow rate of the water was increased in runs 3 and 5 to give a higher water to acrylonitrile ratio. The room temperature flow rates, when corrected for the thermal expansion to the reaction temperature (280° C.), gave a residence time of 0.06 hour (0.2 hour for each reactor).

For runs 2, 4 and 6, the approximate composition (weight percent) of the organic feed to the initial reactor in the series was:

| | |
|---|---|
| acrylonitrile (ACN) | 5 weight percent |
| isobutylene | 27 weight percent |
| monoadduct (MA) | 68 weight percent |

Additional fresh acrylonitrile was fed to the second and third reactors at a rate of 0.75 cc/minute. Water was fed to only the first reactor in series at a rate of 0.75 cc/minute in run 2. The flow rate of the water was increased in runs 4 and 6 to give a higher water to acrylonitrile ratio. The conditions result in a slightly higher overall residence time than for the base runs of 1, 3 and 5. The results of these runs are set forth in Table I.

TABLE I

| | Effect of Separate Addition of Acrylonitrile on Heavies Yield | | | | | | | |
|---|---|---|---|---|---|---|---|---|
| Run No. | Method* of Operation | H$_2$O:ACN Weight Ratio | ACN Conversion % | Yield Based on ACN Converted, % | | | | |
| | | | | MA | Byproduct | DA | MA + DA | Heavies |
| 1 | 1 | 0.5 | 56.0 | 1.2 | 3.7 | 81.7 | 82.9 | 13.4 |
| 2 | 2 | 0.5 | 46.8 | 11.5 | 3.5 | 73.4 | 84.9 | 11.6 |
| 3 | 1 | 1.3 | 54.3 | 7.1 | 4.1 | 79.0 | 86.1 | 9.8 |

TABLE I-continued
Effect of Separate Addition of Acrylonitrile on Heavies Yield

| Run No. | Method* of Operation | H₂O:ACN Weight Ratio | ACN Conversion % | Yield Based on ACN Converted, % | | | | |
|---|---|---|---|---|---|---|---|---|
| | | | | MA | Byproduct | DA | MA + DA | Heavies |
| 4 | 1 | 1.3 | 52.6 | 7.7 | 4.0 | 78.0 | 85.7 | 10.9 |
| 5 | 2 | 1.3 | 39.0 | 2.5 | 5.4 | 82.6 | 85.1 | 8.9 |
| 6 | 2 | 1.3 | 42.0 | 12.4 | 5.3 | 74.3 | 86.7 | 8.0 |

*1 = All acrylonitrile fed to first reactor.
2 = One-third of the fresh acrylonitrile feed fed to each reactor.

As is illustrated in Table I, the introduction of at least a portion of the fresh acrylonitrile feed directly to the second and third reactors resulted in a significantly lower production of undesired heavies.

EXAMPLE II

The following runs were conducted to illustrate the advantage of feeding part of the fresh water to each of the first two reactors in the series rather than feeding the total stream of fresh water to the initial reactor in the series. The reactor system was again three 300 cc high pressure stirred autoclave reactors operating in series. The organic feed to the reactor contained acrylonitrile, isobutylene and monoadduct. Water was fed to either the initial reactor in the series or the first two reactors in the series in a separate stream at a rate to give the desired water to acrylonitrile ratio. All runs were continuous, with data being taken after the reactors had been lined out under simulated recycle conditions with return of the monoadduct to the reactor. Again, the yield of monoadduct was obtained by subtracting the monoadduct fed into the reactors from the monoadduct in the effluent flowing from the reactors. Ideally, the net yield of monoadduct should be zero; however, this was not quite achieved in the runs.

All runs were conducted at a reaction temperature of about 280° C., pressure of about 2500 psig (17 millipascals) and reactor residence time of about 0.6 hour. The approximate composition (weight percent) of the organic feed was:

| | |
|---|---|
| acrylonitrile (ACN) | 13 weight percent |
| isobutylene | 24 weight percent |
| monoadduct (MA) | 63 weight percent |

The organic feed was fed to the first reactor in the series at a rate of 17.8 cc/minute. In run no. 1, fresh water was fed only to the first reactor, with the water feed rate being 2 cc/minute. In run no. 2, fresh water was fed to the first reactor in the series at a rate of 1 cc/minute and likewise to the second reactor in the series at a rate of 1 cc/minute. The results of these runs are set forth in Table II.

TABLE II
Effect of Separate Addition of Water on Middle Byproducts Yield

| Run No. | Method* of Operation | ACN Conversion % | Yield Based on ACn Converted, % | | | | |
|---|---|---|---|---|---|---|---|
| | | | MA | Byproduct | DA | MA + DA | Heavies |
| 1 | 1 | 54.3 | 7.1 | 4.1 | 78.9 | 86.0 | 9.9 |
| 2 | 2 | 51.2 | 9.4 | 2.4 | 77.5 | 86.9 | 10.7 |

*1 = All water fed to first reactor.
2 = One-half of water fed to first reactor and remaining half of water fed to second reactor.

Table II illustrates that a significantly lower amount of undesirable middle byproducts is produced when the water is added to both the first reactor and the second reactor in the series in contrast to adding the water to only the first reactor in the series.

Reasonable variations and modifications are possible within the scope of the foregoing disclosure and the appended claims to the invention.

That which is claimed is:

1. In a process which comprises contacting at least one olefinic hydrocarbon reactant, at least one olefinically unsaturated mononitrile reactant, and at least one monoadduct reaction product of an olefinic hydrocarbon compound and an olefinically unsaturated mononitrile compound, in a plurality of tank reactors in series, in the presence of a diluent, under reaction conditions suitable to produce at least one olefinically unsaturated dinitrile product, each of said olefinically unsaturated mononitrile reactant and said olefinically unsaturated mononitrile compound containing at least one hydrogen atom attached to a doubly bonded carbon atom and containing a cyano group attached to a carbon atom adjacent and doubly bonded to a carbon atom which is attached to at least one hydrogen atom, each of said olefinic hydrocarbon reactant and said olefinic hydrocarbon compound having at least one olefinic linkage having joined to one of the doubly bonded carbons a carbon atom having at least one hydrogen atom attached thereto, wherein at substantially any point in said plurality of tank reactors in series the concentration of the monoadduct reaction product in the resulting reaction mixture is within the range of about 10 to about 90 weight percent of the total reaction mixture, and wherein any unreacted reactants and the reaction products flow sequentially through said plurality of tank reactors in series;

a method for reducing the production of undesired heavy byproducts comprising the step of introducing a portion of said at least one olefinically unsaturated mononitrile compound directly into at least one of said plurality of tank reactors in series other than the initial tank reactor in the series of tank reactors.

2. A process in accordance with claim 1 wherein said undesired heavy byproducts comprise reaction products which have a boiling point greater than the boiling point of said at least one olefinically unsaturated dinitrile product.

3. A process in accordance with claim 2 wherein substantially equal quantities of said at least one olefinically unsaturated mononitrile compound are introduced directly into each one of said plurality of tank reactors in series.

4. A process in accordance with claim 2 wherein said plurality of tank reactors in series comprises three tank reactors in series.

5. A process in accordance with claim 4 wherein each one of said plurality of tank reactors is a stirred tank reactor.

6. A process in accordance with claim 4 wherein approximately one-third of said at least one olefinically unsaturated mononitrile compound is introduced directly into each one of said three tank reactors in series.

7. A process in accordance with claim 1 additionally comprising the step of introducing a portion of said diluent directly into at least one of said plurality of tank reactors in series other than said initial tank reactor in the series of tank reactors to thereby reduce the production of undesired middle byproducts.

8. A process in accordance with claim 7 wherein said undesired middle byproducts comprise reaction products which have boiling points greater than the boiling point of said at least one monoadduct reaction product of an olefinic hydrocarbon compound and an olefinically unsaturated mononitrile compound but less than the boiling point of said at least one olefinically unsaturated dinitrile product.

9. A process in accordance with claim 8 wherein approximately one-half of said diluent is supplied to said initial tank reactor in the series of tank reactors and approximately one-half of said diluent is supplied directly to the second tank reactor in the series of tank reactors.

10. A process in accordance with claim 1 wherein each of said at least one olefinic hydrocarbon reactant and said olefinic hydrocarbon compound is free of acetylenic unsaturation and has from 3 to 18 carbon atoms per molecule with from 1 to 2 ethylenically unsaturated, nonconjugated double bonds as the sole aliphatic unsaturation.

11. A process in accordance with claim 10 wherein each of said at least one olefinically unsaturated mononitrile reactant and said olefinically unsaturated mononitrile compound is free of acetylenic unsaturation, has from 1 to 2 ethylenically unsaturated, nonconjugated double bonds as the sole aliphatic unsaturation, and has from 3 to 18 carbon atoms per molecule.

12. A process in accordance with claim 11 wherein each of said at least one olefinic hydrocarbon reactant and said olefinic hydrocarbon compound is represented by the formula $R'_2C=CR'—CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound is represented by the formula $RCH=CR—CN$ wherein each $R$ is independently selected from the group consisting of hydrogen and hydrocarbyl radicals.

13. A process in accordance with claim 12 wherein said reaction conditions comprise a temperature in the range of about 240° C. to about 350° C., a pressure in the range of about 1000 to about 4000 psig, a contact time in the range of about 30 minutes to about 10 hours, and a mole ratio of said olefinically unsaturated mononitrile reactant to said olefinic hydrocarbon reactant in the range of about 5:1 to about 0.2:1; and wherein said at least one monoadduct reaction product comprises compounds having the structural formula

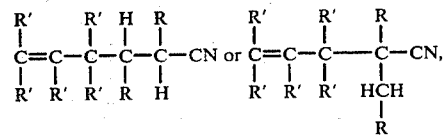

wherein $R$ and $R'$ are as defined above; and further comprising recovering from the resulting reaction effluent said at least one olefinically unsaturated dinitrile reaction product.

14. A process in accordance withh claim 12 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

15. A process in accordance with claim 14 wherein said diluent comprises at least 50 weight percent water; the balance, if any, of said diluent being nonreactive with the reactants and the reactant products.

16. A process in accordance with claim 15 wherein at substantially any point in said plurality of tank reactors in series said concentration of monoadduct reaction product in said reaction mixture is maintained within the range of about 20 to about 80 weight percent.

17. A process in accordance with claim 16 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

18. A process in accordance with claim 1 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

19. A process in accordance with claim 18 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

20. A process in accordance with claim 1 wherein each of said at least one olefinic hydrocarbon reactant and said olefinic hydrocarbon compound has from 3 to 18 carbon atoms and is represented by the formula $R'_2C=CR'—CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula $RCH=CR—CN$ wherein each $R$ is independently selected from the group consisting of hydrogen and hydrocarbyl radicals.

21. A process in accordance with claim 20 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1; and wherein said diluent comprises at least 50 weight percent water; the balance; if any, of said diluent being nonreactive with the reactants and the reaction products; the amount of saiid diluent being in the range of about 0.01 to about 40 parts by weight per part by weight of said at least one olefinically unsaturated mononitrile reactant.

22. In a process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in a plurality of tank reactors in series in the presence of a diluent, under reaction conditions suitable to produce at least one olefinically unsaturated dinitrile product;

wherein each of said at least one olefinic hydrocarbon reactant and said olefinic hydrocarbon compound has from 3 to 18 carbon atoms and is represented by the formula $R'_2C=CR'—CHR'_2$, wherein each $R'$ is independently selected from the group consisting of hydrogen and hydrocarbyl radicals; and wherein each of said at least one olefinically unsaturated mononitrile compound has from 3 to 18 carbon atoms and is represented by the formula $RCH=CR—CN$, wherein each R is independently selected from the group consisting of hydrogen and hydrocarbyl radicals;

wherein said at least one monoadduct reaction product comprises compounds having the structural formula

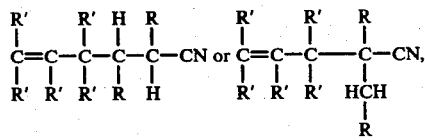

wherein R and R' are as defined above;

wherein said at least one olefinically unsaturated dinitrile product is formed by the monoaddition of a said olefinically unsaturated mononitrile reactant and said monoadduct reaction product;

wherein the amount of said diluent is in the range of about 0.01 to about 40 parts by weight per part by weight of said at least one olefinically unsaturated mononitrile reactant;

wherein said reaction conditions comprise a temperature in the range of about 100° C. to about 500° C., a pressure in the range of about atmospheric to about 100,000 psig, and a liquid hourly space velocity in the range of about 0.05 to about 20;

wherein the mol ratio of said at least one olefinically unsaturated mononitrile reactant to said at least one olefinic hydrocarbon reactant is in the range of about 10:1 to about 0.1:1;

wherein at substantially any point in said plurality of tank reactors in series the concentration of said monoadduct reaction product in the resulting reaction mixture is within the range of about 10 to about 90 weight percent of the total reaction mixture; and wherein any unreacted reactants and the reaction products flow sequentially through said plurality of tank reactors in series;

a method for reducing the production of undesired heavy byproducts comprising the step of introducing a portion of said at least one olefinically unsaturated mononitrile compound directly into at least one of said plurality of tank reactors in series other than the initial tank reactor in the series of tank reactors.

23. A process in accordance with claim 22 wherein said undesired heavy byproducts comprise reaction products which have a boiling point greater than the boiling point of said at least one olefinically unsaturated dinitrile product.

24. A process in accordance with claim 23 wherein substantially equal quantities of said at least one olefinically unsaturated mononitrile compound are introduced directly into each one of said plurality of tank reactors in series.

25. A process in accordance with claim 23 wherein said plurality of tank reactors in series comprises three tank reactors in series.

26. A process in accordance with claim 25 wherein each one of said plurality of tank reactors is a stirred tank reactor.

27. A process in accordance with claim 25 wherein approximately one-third of said at least one olefinically unsaturated mononitrile compound is introduced directly into each one of said three tank reactors in series.

28. A process in accordance with claim 22 additionally comprising the step of introducing a portion of said diluent into at least one of said plurality of tank reactors in series other than said initial tank reactor in the series of tank reactors to thereby reduce the production of undesired middle byproducts.

29. A process in accordance with claim 28 wherein said undesired middle byproducts comprise reaction products which have boiling points greater than the boiling point of said at least one monoadduct reaction product of an olefinic hydrocarbon compound and an olefinically unsaturated mononitrile compound but less than the boiling point of said at least one olefinically unsaturated dinitrile product.

30. A process in accordance with claim 29 wherein approximately one-half of said diluent is supplied to said initial tank reactor in the series of tank reactors and approximately one-half of said diluent is supplied directly to the second trank reactor in the series of tank reactors.

31. A process in accordance with claim 22 wherein said diluent comprises at least 50 weight percent water; the balance, if any, of said diluent being nonreactive with the reactants and the reactant products.

32. A process in accordance with claim 31 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

33. A process in accordance with claim 32 further comprising recovering from the resulting reaction effluent said at least one olefinically unsaturated dinitrile reaction product.

34. A process in accordance withh claim 22 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

35. In a process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in a plurality of tank reactors in series in the presence of a diluent, under reaction conditions suitable to produce at least one olefinically unsaturated dinitrile product, each of said olefinically unsaturated mononitrile reactant and said olefinically unsaturated mononitrile compound containing at least one hydrogen atom attached to a doubly bonded carbon atom and containing a cyano group attached to a carbon atom adjacent and doubly bonded to a carbon atom which is attached to at least one hydrogen atom, each of said olefinic hydrocarbon reactant and said olefinic hydrocarbon compound having at least one olefinic linkage having joined to one of the doubly bonded carbons a carbon atoms having at least one hydrogen atom attached thereto, wherein at substantially any point in said plurality of tank reactors in series the concentration of said monoadduct reaction product in the resulting reaction mixture is within the range of about 10 to about 90 weight percent of the total reaction mixture, and wherein any unreacted reactants and the reaction products flow sequentially through said plurality of tank reactors in series;
  a method for reducing the production of undesired middle byproducts comprising the step of introducing a portion of said diluent directly into at least one of said plurality of tank reactors in series other than the initial tank reactor in the series of tank reactors.

36. A process in accordance with claim 35 wherein said undesired middle byproducts comprise reaction products which have boiling points greater than the boiling point of said at least one monoadduct reaction product of an olefinic hydrocarbon compound and an olefinically unsaturated mononitrile compound but less than the boiling point of said at least one olefinically unsaturated dinitrile product.

37. A process in accordance with claim 36 wherein approximately one-half of said diluent is supplied to said initial tank reactor in the series of tank reactors and approximately one-half of said diluent is supplied directly to the second tank reactor in the series of tank reactors.

38. A process in accordance with claim 37 wherein said plurality of tank reactors in series comprises three tank reactors in series.

39. A process in accordance with claim 38 wherein said plurality of tank reactors comprise stirred tank reactors.

40. A process in accordance with claim 35 wherein each of said at least one olefinic hydrocarbon reactant and said olefinic hydrocarbon compound is free of acetylenic unsaturation and has from 3 to 18 carbon atoms per molecule with from 1 to 2 ethylenically unsaturated, nonconjugated double bonds as the sole aliphatic unsaturation.

41. A process in accordance with claim 40 wherein each of said at least one olefinically unsaturated mononitrile reactant and said olefinically unsaturated mononitrile compound is free of acetylenic unsaturation, has from 1 to 2 ethylenically unsaturated, nonconjugated double bonds as the sole aliphatic unsaturation, and has from 3 to 18 carbon atoms per molecule.

42. A process in accordance with claim 41 wherein each of said at least one olefinic hydrocarbon reactant and said olefinic hydrocarbon compound is represented by the formula $R'_2C=CR'-CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound is represented by the formula $RCH=CR-CN$ wherein each $R$ is independently selected from the group consisting of hydrogen and hydrocarbyl radicals.

43. A process in accordance with claim 42 wherein said reaction conditions comprise a temperature in the range of about 240° C. to about 350° C., a pressure in the range of about 1000 to about 4000 psig, a contact time in the range of about 30 minutes to about 10 hours, and a mole ratio of said olefinically unsaturated mononitrile reactant to said olefinic hydrocarbon reactant in the range of about 5:1 to about 0.2:1; and wherein said at least one monoadduct reaction product comprises compounds having the structural formula

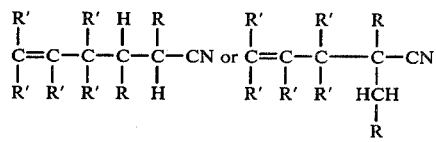

wherein R and R' are as defined above; and further comprising recovering from the resulting reaction effluent said at least one olefinically unsaturated dinitrile reaction product.

44. A process in accordance with claim 42 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

45. A process in accordance with claim 44 wherein said diluent comprises at least 50 weight percent water; the balance, if any, of said diluent being nonreactive with the reactants and the reactant products.

46. A process in accordance with claim 45 wherein at substantially any point in said plurality of tank reactors in series said concentration of monoadduct reaction product in said reaction mixture is maintained within the range of about 20 to about 80 weight percent.

47. A process in accordance with claim 46 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

48. A process in accordance with claim 35 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

49. A process in accordance with claim 48 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

50. A process in accordance with claim 1 wherein each of said at least one olefinic hydrocarbon reactant and said olefinic hydrocarbon compound has from 3 to 18 carbon atoms and is represented by the formula $R'_2C\!=\!CR'\!-\!CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula $RCH\!=\!CR\!-\!CN$ wherein each R is independently selected from the group consisting of hydrogen and hydrocarbyl radicals.

51. A process in accordance with claim 50 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1; and wherein said diluent comprises at least 50 weight percent water; the balance; if any, of said diluent being nonreactive with the reactants and the reaction products; the amount of said diluent being in the range of about 0.01 to about 40 parts by weight per part by weight of said at least one olefinically unsaturated mononitrile reactant.

52. In a process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in a plurality of tank reactors in series in the presence of a diluent, under reaction conditions suitable to produce at least one olefinically unsaturated dinitrile product;

wherein each of said at least one olefinic hydrocarbon reactant and said olefinic hydrocarbon compound has from 3 to 18 carbon atoms and is represented by the formula $R'_2C\!=\!CR'\!-\!CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula $RCH\!=\!CR\!-\!CN$, wherein each R is independently selected from the group consisting of hydrogen and hydrocarbyl radicals;

wherein said at least one monoadduct reaction product comprises compounds having the structural formula

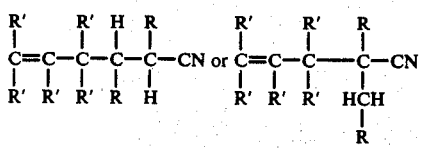

wherein R and R' are as defined above;
wherein said at least one olefinically unsaturated dinitrile product is formed by the monoaddition of a said olefinically unsaturated mononitrile reactant and said monoadduct reaction product;

wherein the amount of said diluent is in the range of about 0.01 to about 40 parts by weight per part by weight of said at least one olefinically unsaturated mononitrile reactant;

wherein said reaction conditions comprise a temperature in the range of about 100° C. to about 500° C., a pressure in the range of about atmospheric to about 100,000 psig, and a liquid hourly space velocity in the range of about 0.05 to about 20;

wherein the mol ratio of said at least one olefinically unsaturated mononitrile reactant to said at least one olefinic hydrocarbon reactant is in the range of about 10:1 to about 0.1:1;

wherein at substantially any point in said plurality of tank reactors in series the concentration of said monoadduct reaction product in the resulting reaction mixture is within the range of about 10 to about 90 weight percent of the total reaction mixture; and wherein any unreacted reactants and the reaction products flow sequentially through said plurality of tank reactors in series;

a method for reducing the production of undesired middle byproducts comprising the step of introducing a portion of said diluent directly into at least one of said plurality of tank reactors in series other than the initial tank reactor in the series of tank reactors.

53. A process in accordance with claim 52 wherein said undesired middle byproducts comprise reaction products which have boiling points greater than the boiling point of said at least one monoadduct reaction product of an olefinic hydrocarbon compound and an olefinically unsaturated mononitrile compound but less than the boiling point of said at least one olefinically unsaturated dinitrile product.

54. A process in accordance with claim 53 wherein approximately one-half of said diluent is supplied to said initial tank reactor in the series of tank reactors and approximately one-half of said diluent is supplied directly to the second tank reactor in the series of tank reactors.

55. A process in accordance with claim 54 wherein said plurality of tank reactors in series comprises three tank reactors in series.

56. A process in accordance with claim 55 wherein said plurality of tank reactors comprise stirred tank reactors.

57. A process in accordance with claim 52 wherein said diluent comprises at least 50 weight percent water; the balance, if any, of said diluent being nonreactive with the reactants and the reactant products.

58. A process in accordance with claim 57 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

59. A process in accordance with claim 58 further comprising recovering from the resulting reaction effluent said at least one olefinically unsaturated dinitrile reaction product.

60. A process in accordance with claim 52 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

* * * * *